US008825144B2

(12) United States Patent
Starks

(10) Patent No.: US 8,825,144 B2
(45) Date of Patent: *Sep. 2, 2014

(54) CARDIAC MAPPING SYSTEM AND METHOD

(71) Applicant: St. Jude Medical, Atrial Fibrillation Division, Inc., St. Paul, MN (US)

(72) Inventor: Daniel R. Starks, Lake Elmo, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 51 days.

This patent is subject to a terminal disclaimer.

(21) Appl. No.: 13/710,156

(22) Filed: Dec. 10, 2012

(65) Prior Publication Data

US 2014/0005528 A1 Jan. 2, 2014

Related U.S. Application Data

(63) Continuation of application No. 12/743,629, filed as application No. PCT/US2008/087269 on Dec. 17, 2008, now Pat. No. 8,352,019.

(60) Provisional application No. 61/014,135, filed on Dec. 17, 2007.

(51) Int. Cl.
*A61B 5/04* (2006.01)
*A61B 5/042* (2006.01)
*A61B 6/12* (2006.01)
*A61B 5/06* (2006.01)
*A61B 6/00* (2006.01)

(52) U.S. Cl.
CPC . *A61B 6/12* (2013.01); *A61B 5/042* (2013.01); *A61B 5/06* (2013.01); *A61B 6/503* (2013.01)
USPC .......................................... 600/509

(58) Field of Classification Search
USPC .......... 600/374, 424, 433–435, 509, 512, 523
See application file for complete search history.

(56) References Cited

U.S. PATENT DOCUMENTS

| 5,297,549 | A  | 3/1994  | Beatty et al.    |
| 5,480,422 | A  | 1/1996  | Ben-Haim et al.  |
| 5,568,809 | A  | 10/1996 | Ben-Haim et al.  |
| 5,662,108 | A  | 9/1997  | Budd et al.      |
| 5,687,737 | A  | 11/1997 | Branham et al.   |
| 5,697,377 | A  | 12/1997 | Wittkampf        |
| 6,050,267 | A  | 4/2000  | Nardella et al.  |
| 6,603,996 | B1 | 8/2003  | Beatty et al.    |

(Continued)

OTHER PUBLICATIONS

Early, Mark J., et al. "Radiofrequency Ablation of Arrhythmias Guided by Non-Fluoroscopic Catheter Location: A Prospective Randomized Trial", European Heart Journal, vol. 27, 2006, pp. 1223-1229.

(Continued)

*Primary Examiner* — Brian T Gedeon
(74) *Attorney, Agent, or Firm* — Trenner Law Firm, LLC

(57) ABSTRACT

Medical navigation and mapping system and methods are disclosed for modeling both unobstructed and obstructed portions of a catheter. An exemplary system includes a rendering component operatively associated with an output device. The rendering component overlays a plurality of data images on one another to generate a three-dimensional image representing both the internal tissue and a visible portion of a catheter body. An enhancement component is configured to overlay a silhouette on the three-dimensional image. The silhouette represents an obstructed portion of the catheter body.

20 Claims, 9 Drawing Sheets

(56) References Cited

U.S. PATENT DOCUMENTS

| | | |
|---|---|---|
| 6,640,119 B1 | 10/2003 | Budd et al. |
| 6,650,927 B1 | 11/2003 | Keidar |
| 6,892,091 B1 | 5/2005 | Ben-Haim et al. |
| 7,505,810 B2 | 3/2009 | Harlev et al. |
| 7,937,136 B2 | 5/2011 | Harlev et al. |
| 2004/0254437 A1 | 12/2004 | Hauck et al. |

OTHER PUBLICATIONS

Paul, Thomas, et al., "Atrial Reentrant Tachycardia After Surgery for Congenital Heart Disease: Endocardial Mapping and Radiofrequency Catheter Ablation Using a Novel, Noncontact Mapping System", Circulation, vol. 103, 2001, 2266-2271.

Verma, et al., Real-Time, Three-Dimensional Localization of a Brockenbrough Needle During Transseptal Catheterization Using a Nonfluoroscopic Method (Verma, et al.) Journal of Invasive Cardiology, vol. 8, Issue 7; http://www.invasivecardiology.com/article15858 Jul. 1, 2006.

CARDIAC MAPPING SYSTEM AND METHOD

CROSS-REFERENCE TO RELATED APPLICATIONS

This application is a continuation of U.S. patent application Ser. No. 12/743,629 titled "Systems and methods for modeling both unobstructed and obstructed portions of a catheter" of Daniel R. Starks, et al. (the '629 application) filed on 19 May 2010, now U.S. Pat. No. 8,352,019, which claims the benefit of international application no. PCT/US2008/087269 (the '269 application), filed 17 Dec. 2008, which claims the benefit of and priority to U.S. provisional application No. 61/014,135, filed 17 Dec. 2007 (the '135 application). The '629 application, '269 application, and '135 application are each hereby incorporated by reference as though fully set forth herein.

BACKGROUND OF THE INVENTION a. Field of the Invention

The instant invention relates to electrical mapping of a patient's heart. In particular, the instant invention relates to a catheter which gathers data for high resolution cardiac mapping and associated components which generate a model showing a graphical representation of the heart and catheter even if portions of the catheter would otherwise be obstructed from view.

b. Background Art

A number of mapping and navigation options are available for electrical mapping of a patient's heart, for example, to navigate a catheter to a desired site within the patient's heart for an ablation or other medical procedure. For example, the EnSite NavX® utility is integrated into the Ensite® Advanced Mapping System (available from St. Jude Medical, Inc.), and provides non-fluoroscopic navigation of electrophysiology catheters.

The methodology implemented by this mapping system is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

These six surface electrodes are connected to the Ensite® Advanced Mapping System, which alternately sends an electrical signal through each pair of surface electrodes to create a voltage gradient along each of the three axes, forming a transthoracic electrical field. Conventional electrophysiology catheters may be connected to the Ensite® Advanced Mapping System and advanced to the patient's heart. As a catheter enters the transthoracic field, each catheter electrode senses voltage, timed to the creation of the gradient along each axis. Using the sensed voltages compared to the voltage gradient on all three axes, the EnSite NavX® utility calculates the three-dimensional position of each catheter electrode. The calculated position for the various electrodes occurs simultaneously and repeats many times per second (e.g., about 93 times per second).

The Ensite® Advanced Mapping System displays the located electrodes as catheter bodies with real-time navigation. By tracking the position of the various catheters, the EnSite NavX® utility provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers.

Once the mapping data has been acquired, software may be implemented to generate multiple surface images, which when combined, comprise a three-dimensional image of the patient's heart. This image can be displayed on a suitable output device in real-time so that the physician can "see" the patient's heart and the catheter for properly positioning the catheter at a work site within the patient's heart for a medical procedure (e.g., an ablation procedure). However, the rendering techniques used to generate the three-dimensional image of the patient's heart necessarily result in portions of the catheter being obscured. For example, the catheter may be physically located "behind" the surface of the heart being viewed, and therefore portions of the catheter may be obscured from view in the rendered three-dimensional image. Or for example, the catheter may be drawn behind other objects being displayed for the physician, such as labels or other graphical entities.

By way of illustration, Ensite® Advanced Mapping System creates computer models of heart chambers which are then displayed graphically on the computer screen. Simultaneously, one or more catheters are also displayed in the corresponding position and orientation with respect to the heart chambers. Because the catheters are usually inside the heart chambers, the display of these catheters can be completely or partially obstructed (i.e., obscured from view) by the simultaneous or overlapping display of the heart chamber walls. The catheter can be additionally obscured from view by other graphical entities, such as labels, lesions, anatomical markers, and other catheters. Although the physician may have a good idea of where the catheter is within the heart, there exists a need to provide more clarity for the physician.

BRIEF SUMMARY OF THE INVENTION

It is desirable to be able to provide high-quality images of the patient's heart and catheter for the physician to view during a medical procedure. It is further desirable to be able to provide the physician a graphical rendering or drawing of both the visible or unobstructed portions of the catheter and the visually obstructed portions of the catheter.

The present invention is directed to a high density mapping catheter and associated methods of modeling the catheter on a display outside the patient's body, the model showing both the unobstructed portions of the catheter and the visually obstructed portions of the catheter. In exemplary embodiments, the unobstructed portions of the catheter and the visually obstructed portions of the catheter are shown different from one another so that the physician can easily discern which portions are unobstructed and which portions are obstructed. For example, the unobstructed portion of the catheter may be shown as a 3-D rendering, while the visually obstructed portion of the catheter may be shown in "silhouette" form overlaying (or in the foreground, or "on top of") all other objects being shown on the display. The silhouette is created in piecewise fashion for only those portions of the catheter boundary that are obscured. In other examples, the different portions of the catheter may be different colors, shown as solid versus outline form, etc. In any event, the physician is provided with a clear rendering of the entire length of the catheter that is in the display area.

In accordance with one aspect of the present invention, an electrical mapping system is disclosed for modeling both obstructed and unobstructed portions of a catheter. The system includes a catheter body comprising a distal portion and a proximal portion, the catheter body supporting a plurality of electrodes electrically connected to an output device. The system also includes a processing component operatively associated with the output device. The rendering component receives raw data from the plurality of electrodes and generates a plurality of images based on the raw data. The rendering component overlays the plurality of data images on one another to generate a three-dimensional image representing both the internal tissue and an unobstructed portion of the catheter body. The system also includes a visual enhancement component which overlays a silhouette representing at least one obstructed portion of the catheter body using the positional data for the catheter body.

In accordance with another aspect of the present invention, a catheter system is disclosed for use in electrical mapping of internal tissue. The catheter system includes a catheter body extending between a distal tip and a proximal portion. The catheter body includes a plurality of mapping electrodes supported in the distal tip for use in acquiring mapping information. A rendering component is configured to generate a three-dimensional image based on the mapping information. The three-dimensional image represents an outer boundary of the internal tissue and an unobstructed portion of the catheter body relative to the outer boundary of the internal tissue. A visual enhancement component is configured to overlay a silhouette representing at least one obstructed portion of the catheter body on the three-dimensional image.

In accordance with another aspect of the present invention, a method is disclosed for mapping cardiac tissue and modeling both obstructed and unobstructed portions of an electrode catheter. The method comprises introducing the electrode catheter into a chamber of a heart to be mapped, and moving the electrode catheter relative to a surface of the heart, wherein a plurality of electrodes contact the surface of the heart to generate mapping coordinates. The method also comprises generating a three-dimensional image based on the mapping information, the three-dimensional image representing the surface of the heart and an unobstructed portion of the electrode catheter. The method also comprises determining which portion of the electrode catheter is obstructed, and overlaying the obstructed portion of the electrode catheter on the three-dimensional image.

In accordance with another aspect of the present invention, a method is disclosed for mapping cardiac tissue and modeling both obstructed and unobstructed portions of an electrode catheter. The method comprises obtaining mapping coordinates from the electrode catheter inserted into a chamber of a heart, the mapping coordinates representing a surface of the heart. The method also comprises generating a three-dimensional image based on the mapping information, the three-dimensional image representing the surface of the heart and an unobstructed portion of the electrode catheter. The method also comprises generating a plurality of candidate silhouette fragments representing a body of the electrode catheter, and determining which candidate silhouette fragments are obstructed by other visible objects in the three-dimensional image. The method also comprises overlaying the obstructed portion of the electrode catheter using only those candidate silhouette fragments obstructed by other visible objects in the three-dimensional image.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
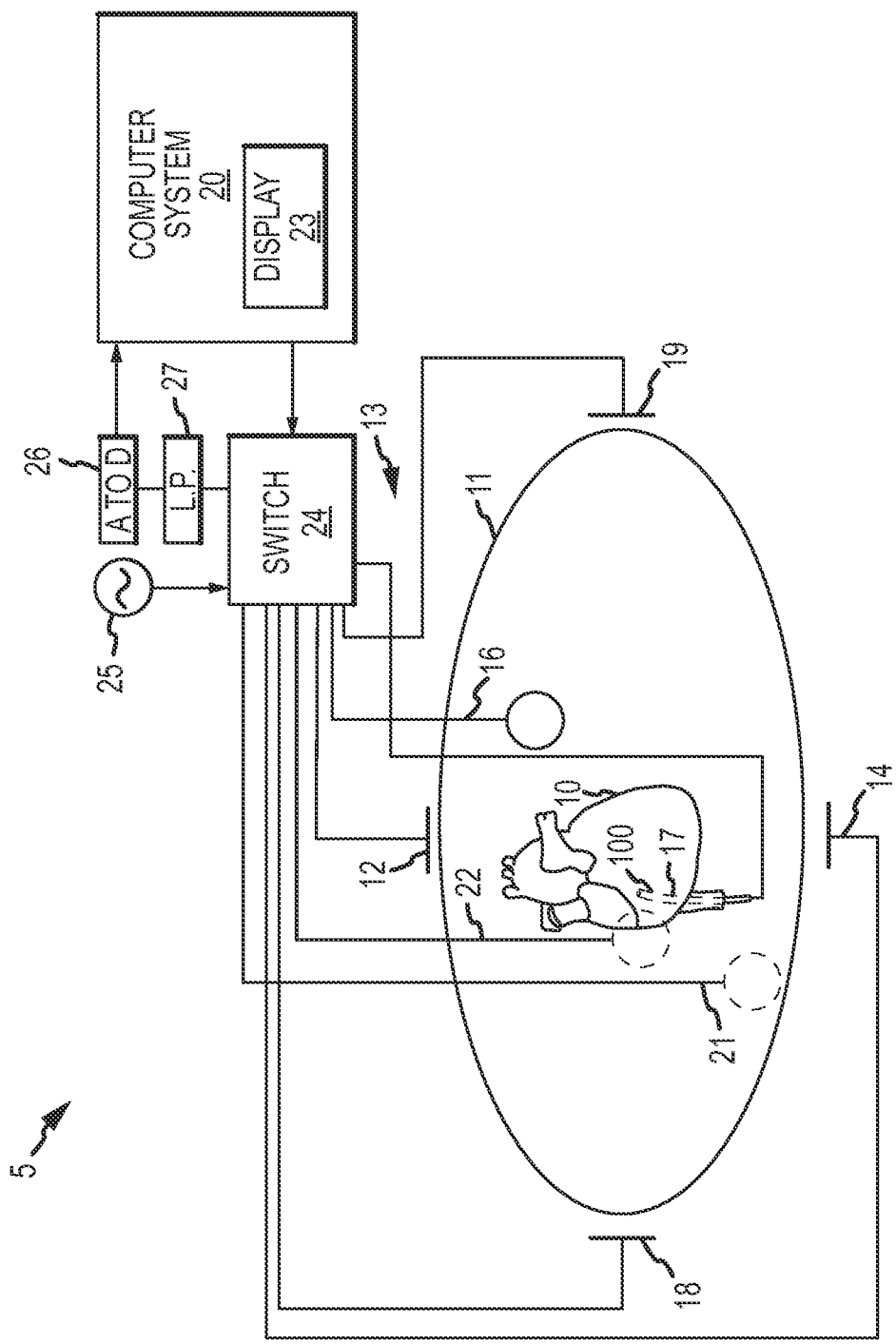
FIG. 1 is a schematic diagram of a navigation and mapping system in accordance with the present invention.

FIG. 1 presents a schematic of one embodiment of a medical navigation/visualization system 5. The medical navigation/visualization system 5 will be briefly addressed herein, as it is one such system that may utilize the mapping electrode functionality that will be addressed in detail below. The medical navigation/visualization system 5 is also discussed in detail in U.S. Patent Application Publication No. US 2004/0254437 (published on Dec. 16, 2004) that is assigned to the assignee of this patent application, and the entire disclosure of which is incorporated by reference in its entirety herein.

The patient 11 is only schematically depicted as an oval for clarity. Three sets of surface or patch electrodes are shown as 18, 19 along a Y-axis; as 12, 14 along an X-axis; and 16, 22 along a Z-axis. Patch electrode 16 is shown on the surface closest to the observer, and patch electrode 22 is shown in outline form to show its placement on the back of patient 11. An additional patch electrode, which may be referred to as a "belly" patch, is also seen in the figure as patch electrode 21.

Each patch electrode 18, 19, 12, 14, 16, 22, 21 is independently connected to a multiplex switch 24. The heart 10 of patient 11 lies between these various sets of patch electrodes 18, 19, 12, 14, 16, 22. Also seen in this figure is a representative catheter 13 having a number of electrodes 17. The electrodes 17 may be referred to as the "roving electrodes" or "measurement electrodes" herein. It is noted that any number of electrodes may be utilized, generally with more electrodes providing higher-density mapping. It is also noted that in use the patient 11 will have most or all of the conventional 12 lead ECG system in place as well, and this ECG information is available to the system even though it is not illustrated in the figures.

Each patch electrode 18, 19, 12, 14, 16, 22, 21 is coupled to the switch 24, and pairs of electrodes 18, 19, 12, 14, 16, 22 are selected by software running on computer system 20, which couples these electrodes 18, 19, 12, 14, 16, 22 to the signal generator 25. A pair of electrodes, for example electrodes 18 and 19, may be excited by the signal generator 25 and they generate a field in the body of the patient and the heart 10. During the delivery of the current pulse, the remaining patch electrodes 12, 14, 16, 22 are referenced to the belly patch electrode 21, and the voltages impressed on these remaining electrodes 12, 14, 16, 22 are measured by the analog-to-digital or A-to-D converter 26. Suitable lowpass filtering of the digital data may be subsequently performed in software to remove electronic noise and cardiac motion artifact after suitable low pass filtering in filter 27. In this fashion, the various patch electrodes 18, 19, 12, 14, 16, 22 are divided into driven and non-driven electrode sets. While a pair of electrodes is driven by the signal generator 25, the remaining non-driven electrodes are used as references to synthesize the orthogonal drive axes.

The belly patch electrode 21 is seen in the figure is an alternative to a fixed intra-cardiac electrode. In many instances, a coronary sinus electrode or other fixed electrode in the heart 10 can be used as a reference for measuring voltages and displacements. All of the raw patch voltage data is measured by the A-to-D converter 26 and stored in the computer system 20 under the direction of software. This electrode excitation process occurs rapidly and sequentially as alternate sets of patch electrodes 18, 19, 12, 14, 16, 22 are selected, and the remaining members of the set are used to measure voltages. This collection of voltage measurements may be referred to herein as the "patch data set". The software has access to each individual voltage measurement made at each individual patch electrode 18, 19, 12, 14, 16, 22 during each excitation of each pair of electrodes 18, 19, 12, 14, 16, 22.

The raw patch data is used to determine the "raw" location in three spaces (X, Y, Z) of the electrodes inside the heart 10, such as the roving electrodes 17. This process is also referred to as "triangulation." Triangulation is the process of determining the location of a point by measuring angles from known points. Optical three-dimensional measuring systems use triangulation networks in order to determine spatial dimensions and the geometry. Output of at least two of the sensors are considered the point on an object's surface which define a spatial triangle. Within this triangle, the distance between the sensors is the base and is known. By determining the angles between the sensors and the basis, the intersection point, and thus the 3d coordinate, is calculated from the triangular relations.

If the roving electrodes 17 are swept around in the heart chamber while the heart 10 is beating, a large number of electrode locations are collected. These data points are taken at all stages of the heartbeat and without regard to the cardiac phase. Since the heart 10 changes shape during contraction, only a small number of the points represent the maximum heart volume. By selecting the most exterior points, it is possible to create a "shell" representing the shape of the heart 10. The location attribute of the electrodes within the heart 10 are measured while the electric field is impressed on the heart 10 by the surface patch electrodes 18, 19, 12, 14, 16, 22. The patch data set may also be used to create a respiration compensation value to improve the raw location data for the locations of the electrodes 18, 19, 12, 14, 16, 22 due to movement of the patient's body (e.g., during breathing).

Figure 2:
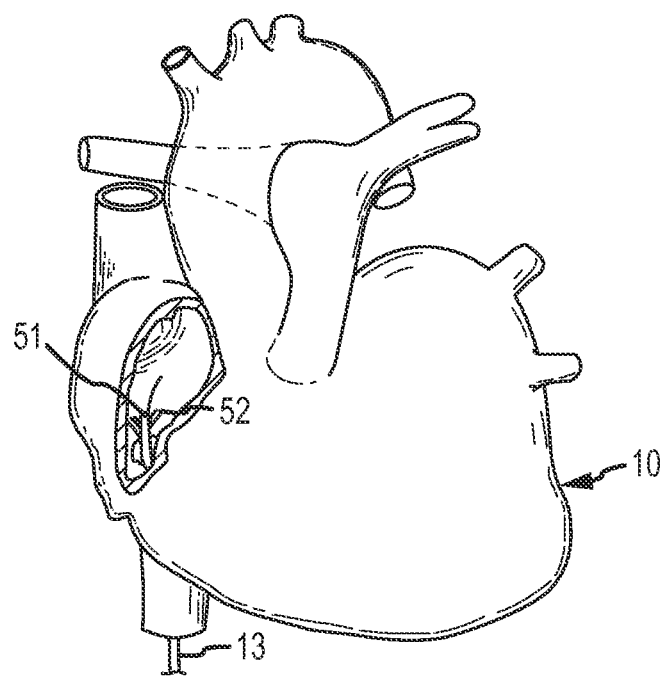
FIG. 2 illustrates a catheter being introduced into a patient's heart.

FIG. 2 shows a catheter 13, which may be a high-density mapping catheter, as described in more detail below, in the heart 10. The catheter 13 has a tip electrode 51 (and may optionally include additional electrodes, not visible in the figures). Since these electrodes lie in the heart 10, the location process detects their location in the heart 10. While they lay on the surface and when the signal generator 25 is "off", each patch electrode 18, 19, 12, 14, 16, 22 (FIG. 1) can be used to measure the voltage on the heart surface. The magnitude of this voltage, as well as the timing relationship of the signal with respect to the heartbeat events, may be measured and presented to the cardiologist or technician through the display 23. The peak-to-peak voltage measured at a particular location on the heart wall is capable of showing areas of diminished conductivity, and which may reflect an infracted region of the heart 10. The timing relationship data are typically displayed as "isochrones". In essence, regions that receive the depolarization waveform at the same time are shown in the same false color or gray scale.

Figure 3:
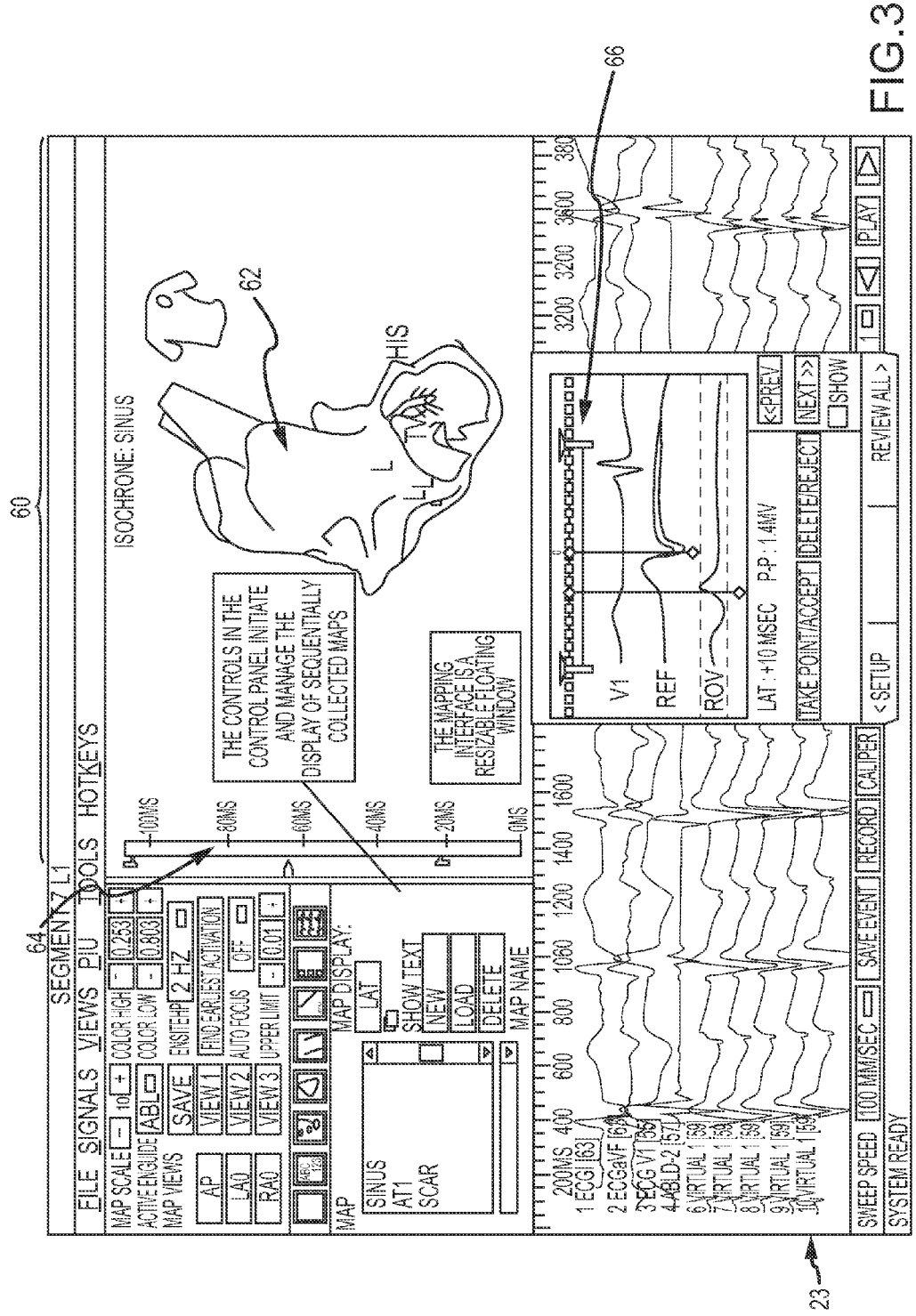
FIG. 3 illustrates a display provided by a navigation and mapping system in accordance with the present invention.

FIG. 3 shows an illustrative computer display from the computer system 20. The display 23 is used to show data to the physician user and to present certain options that allow the user to tailor the system configuration for a particular use. It should be noted that the contents on the display 23 can be easily modified and the specific data presented is only of a representative nature. An image panel 60 shows a geometry of the heart chamber 62 that shows "isochrones" in false color or grayscale together with guide bar 64 to assist in interpretation. In this hypothetical image, the noted mapping methodology has been used with a high-density catheter to create a chamber representation that is displayed as a contoured image.

The guide bar 64 is graduated in milliseconds and it shows the assignment of time relationship for the false color image in the geometry. The relationship between the false color on the geometry image 62 and the guide bar 64 is defined by interaction with the user in panel 66. As shown, the display may also provide traces and other information related to the ECG electrodes, mapping electrodes and reference electrodes, as well as other information that may assist the physicians.

Figure 4:
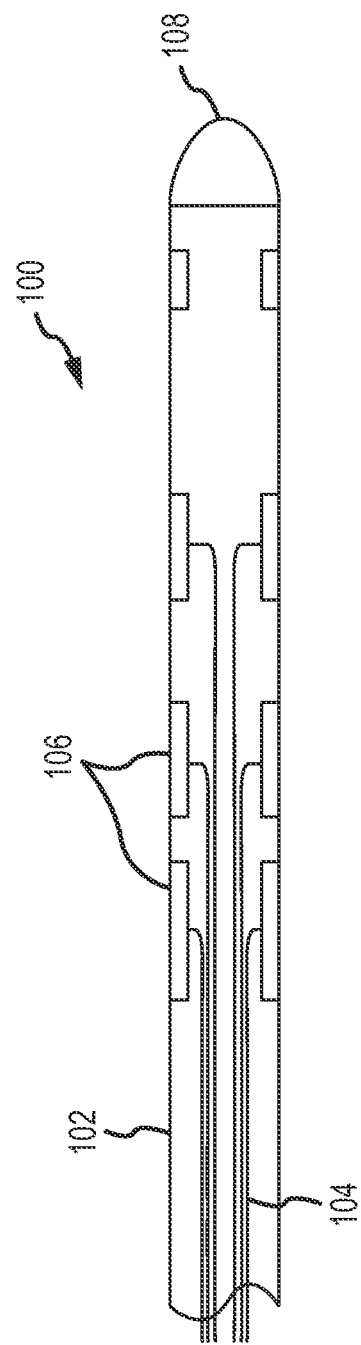
FIG. 4 illustrated an exemplary embodiment of a high density mapping catheter in accordance with the present invention.

As noted above, a significant amount of data is required to generate a detailed image of the cardiac tissue of interest. In order to gather adequate data more quickly, a high density mapping electrode catheter may be implemented having a plurality of electrodes. An exemplary catheter 100 is shown in FIG. 4. The illustrated catheter 100 includes a catheter body or shaft 102 having an electrode tip 108 disposed at a distal end thereof. The catheter 100 further includes a number of mapping electrode wires 104 terminating in electrodes 106. The electrodes 106 can be used to map cardiac tissue, as discussed above. More specifically, a physician can sweep the electrodes 106 across tissue to be mapped. In this regard, a large volume of mapping information can be obtained quickly when the electrodes 106 come into contact with the tissue as the catheter 100 is swept across the tissue.

Each of the wires 104 may be threaded through an inner lumen of the catheter shaft 102. The electrodes 106 then extend through holes formed in the catheter shaft 102 at the desired location. The electrodes 106 may be bonded to the shaft 102 at the openings or may otherwise be maintained in a substantially fixed relationship with respect to the shaft 102.

In exemplary embodiments, the electrodes 106 may be tightly secured to catheter shaft 102. Alternatively, each of the mapping electrodes may be formed from a nickel titanium fiber with a conductive metallic core such as platinum. The conductive core of the illustrated fibers serves as the electrical pathway for the tip electrodes 106 (instead of the wires 104). In such an embodiment, the tip electrodes 106 may be formed by melting an exposed section of the conductive core near the surface of the catheter shaft 102.

Generally, the catheter shaft 102 will have a diameter and stiffness that is significantly greater than the diameter and stiffness of the wiring 104 provided therein. For instance, the catheter shaft 102 may be a 5 or 7 French (i.e., 0.065 in. or 0.092 in.) catheter. In such embodiments, the catheter shaft may have a diameter that is at least five to ten times (or more) the diameter of the individual wires 104. The size of the catheter shaft 102 may allow the catheter shaft 102 to readily deflect when the moved (e.g., brushed) over an internal tissue surface without significant deflection of the catheter shaft 102. For instance, the catheter shaft may have a buckle strength (e.g., where bending is initiated) of no more than about 5 grams and more preferably no more than about 1-2 grams. Use of such low buckling strength allows the end of the catheter shaft 102 to readily conform to a tissue surface without significantly deflecting or otherwise penetrating the tissue surface. In addition, when the catheter shaft contacts an internal tissue surface, the stiffness of the shaft alerts an operator (e.g., physician) that the catheter shaft is in contact with patient tissue.

As mentioned above, the inner lumen of the catheter shaft 102 may be used to thread the wiring 104 for the electrodes 106. In addition, for certain procedures, it may be desired to irrigate the electrodes 106 with saline solution, for example, to prevent undesired heating or clotting. A lumen for such irrigation fluid may be formed within catheter shaft 102 (which can include openings to allow for flow of the irrigation fluid), or the irrigation fluid may be delivered via a separate lumen associated with other structure of the catheter.

It is desirable to provide an enlarged, generally spherical tip of the catheter. This tip configuration has a number of advantages. First, it is desirable to avoid puncturing of the cardiac tissue in connection with contact by the catheter. The enlarged and rounded configuration of the tip in this regard provides a larger surface contact area and reduces the pressure on and likelihood of puncturing any cardiac tissue contacted. In addition, it is desirable to enhance the visibility of the tip, both on the mapping display and in connection with any fluoroscopic images obtained in connection with the procedure. The enlarged tip improves impedance and, therefore, visibility with respect to the electrical navigation system. The increased cross-section also improves visibility with respect to the fluoroscopic images.

While the catheter 100 described above with reference to the figures represents an advantageous implementation of the present invention, it will be appreciated that many other implementations are also possible.

The electrodes 106 can be any of various types of electrodes including ablation electrodes, mapping electrodes, or combination ablation/mapping electrodes. The illustrated electrodes 106 are mapping electrodes, as best shown in FIG. 4. The electrodes 106 are divided into a number of electrically isolated sections 110, in this case, defining four quadrants. Because the sections 110 are electrically isolated, independent positioning signals can be obtained with regard to each of the sections 110. In this manner the signals from the sections 110 can be processed to define references, e.g., North, South, East and West, which are useful in guiding movement of the catheter during a medical procedure.

Figure 5:
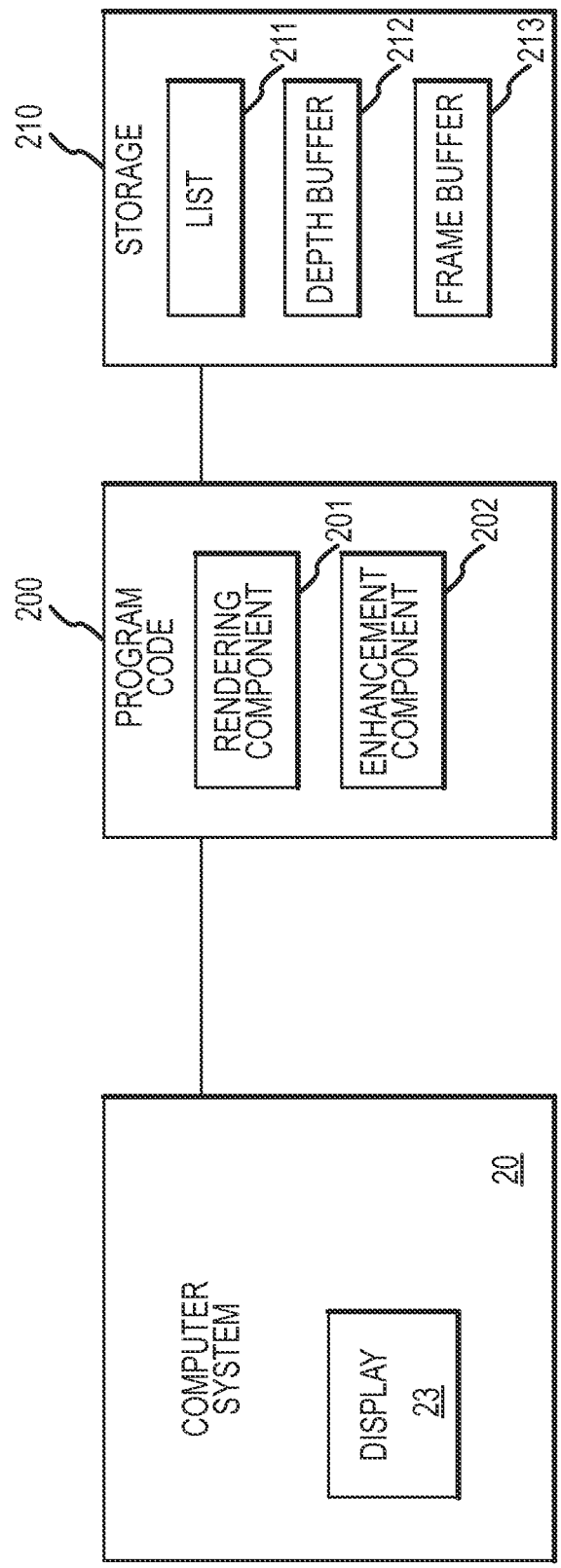
FIG. 5 is a block diagram illustrating an exemplary embodiment of computer components and program code which may be implemented in accordance with the present invention.

FIG. 5 is a block diagram illustrating an exemplary embodiment of computer components and program code which may be implemented in accordance with the present invention to process the positional or mapping data from the electrodes 106. The mapping data obtained by the electrodes 106 may be processed using software 200 executable on a computer system (e.g., the computer system 20 shown in FIG. 1). In an exemplary embodiment, the software 200 may include a rendering component 201 and an enhancement component 202, each operatively associated with an output device (e.g., the display 23 in FIG. 1) and computer readable storage 210. The processing component 201 receives raw data from the electrodes 106 and generates a plurality of images based on the raw data. The rendering component 201 may overlay the data images on one another to generate a three-dimensional image representing both the internal tissue and an unobstructed portion of the catheter body. Exemplary output is illustrated in FIG. 6A-C, and discussed in more detail below.

Figure 6A:
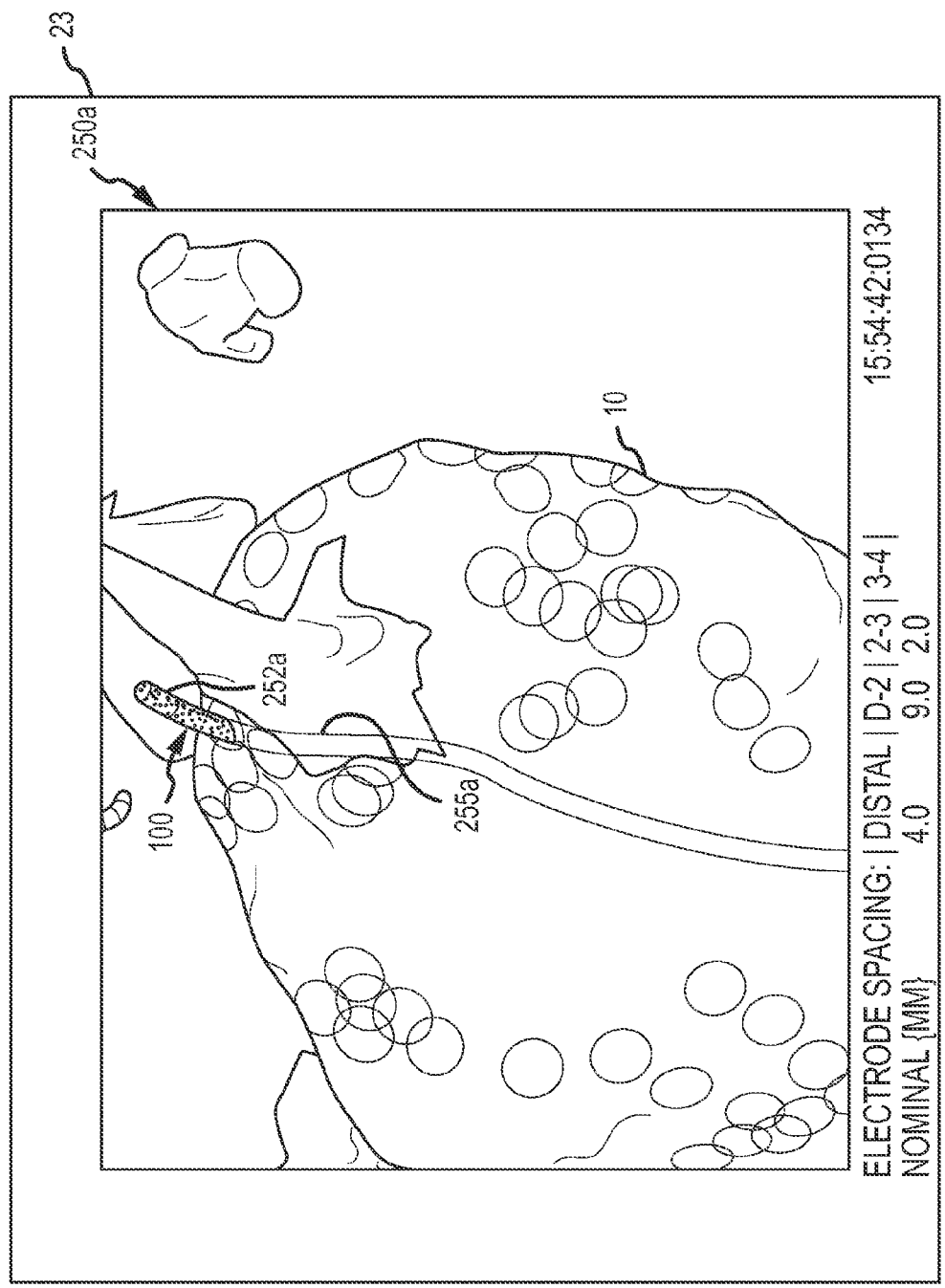
FIG. 6A-C illustrate exemplary images which may be output on a display provided by the navigation and mapping system, wherein a graphical rendering or drawing of the catheter showing both unobstructed and what would otherwise be obstructed portions of a catheter.
Figure 6B:
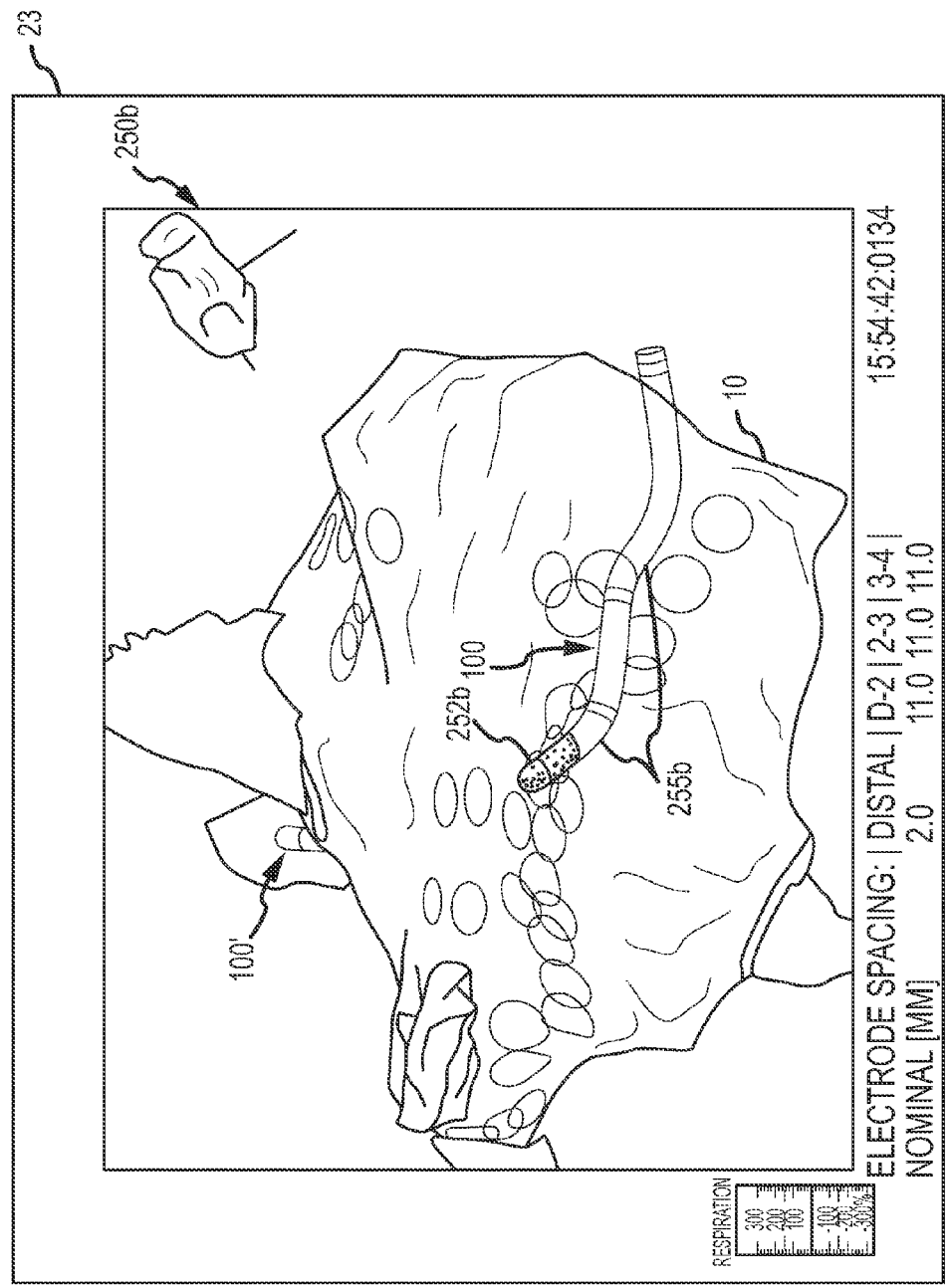
Figure 6C:
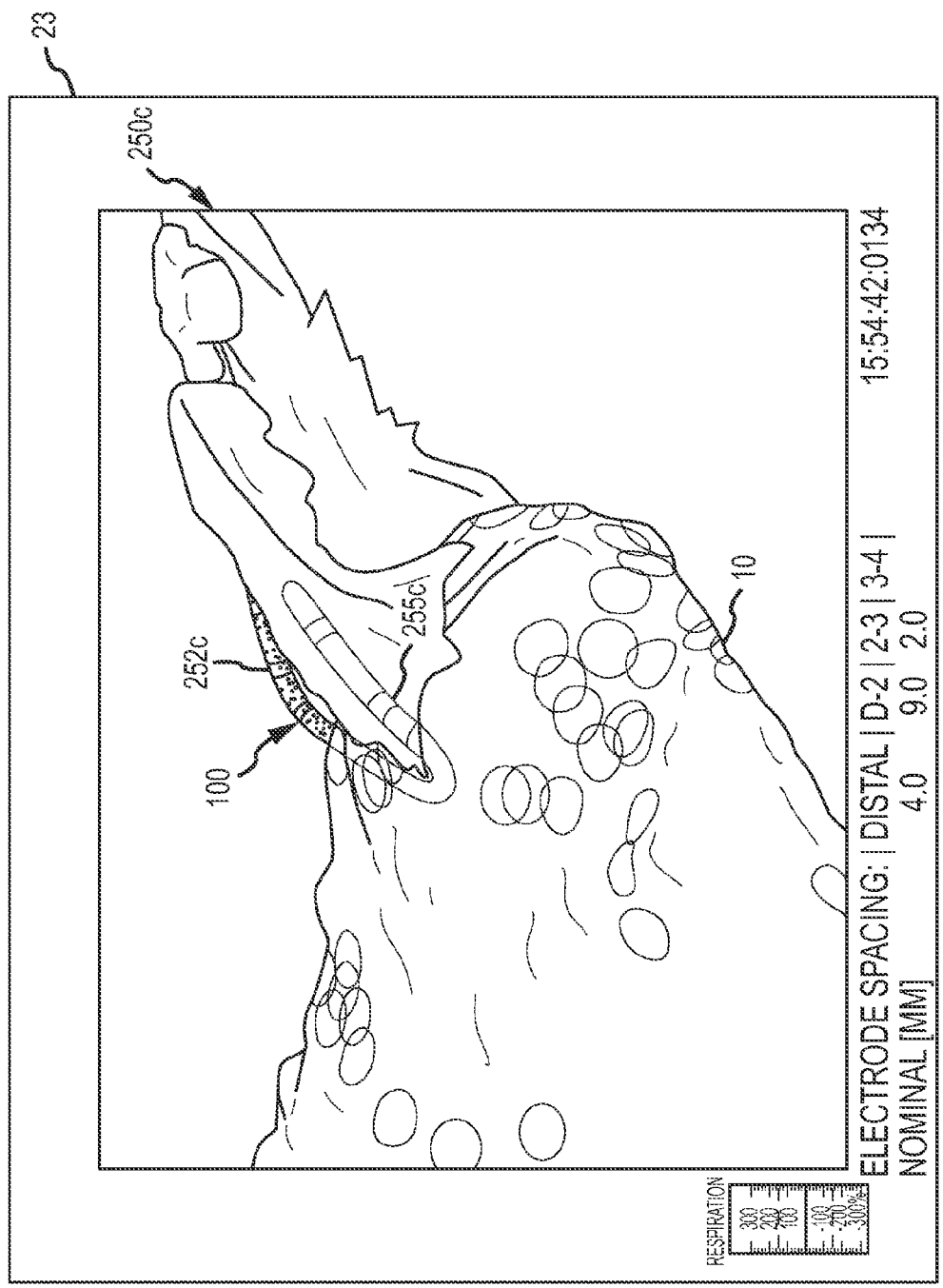

The enhancement component 202 overlays a silhouette of what would otherwise be an obstructed portion of the catheter body 102 using the positional data for the catheter body 102 (e.g., as can be seen in FIG. 6A-C). Operation of the enhancement component 202 may be described as including two tasks. First, the enhancement component 202 generates candidate silhouette fragments, and second the enhancement component 202 displays only those candidate fragments that are obscured or obstructed by other objects in the scene output on the display 23.

The first task may be accomplished using the same triangulation data that are used to produce the three-dimensional image of the catheter (e.g., as used by the processing component 201). The triangles are joined edge-to-edge to form a closed volume that approximates very closely the true shape of the body of the catheter. Candidate silhouette fragments are those edges shared between two triangles, one with its outward side pointing toward the physician's field of view, and the other with its outward side pointing away from the physician's field of view.

Each of the candidate edges may be compiled into a list 211 for further processing. Additional edges may be added in special cases. One such special case may include when the edge separates a catheter electrode 106 from the catheter body 102 and at least one of the adjacent triangles has an outward side pointing toward the physician's field of view. Another such case may include when the edge is at the end of the catheter body 102 and the end plane has its outward side pointing toward the physician's field of view. Another such case may include when the edge is at the end of the catheter body 102 and the adjacent triangle has its outward side pointing toward the physician's field of view.

The second task may be accomplished by applying a graphics depth buffer 212. Each edge in the list of candidate silhouette fragments is first offset away from the center of the catheter body 102 by a distance in the model space corresponding to one pixel on the display 23. This avoids the possibility of the edge being obscured by the same catheter body 102 that generated the edge. The edge is then drawn into a frame buffer 213 using a depth mask that allows drawing of a pixel only if the depth is greater than the current depth.

After completing these tasks, the visual enhancement component is able to overlay a silhouette representing at least one obstructed portion of the catheter body using the positional data for the catheter body. FIG. 6A-C illustrate exemplary images 250a-c which may be output on a display provided by the navigation and mapping system, such as the display 23 shown in FIGS. 1 and 3. In FIG. 6A-C, a graphical rendering of the catheter 100 includes both an unobstructed portion 252a-c (respectively in FIG. 6A-C) and portion 255a-c of the catheter 100 that would otherwise be obstructed from view (e.g., behind the heart wall). Accordingly, the physician is able to view an image of the entire length of the catheter 100 which is within the area being displayed.

In FIG. 6A-C, both the unobstructed portions 252a-c (respectively) of the catheter 100, and the obstructed portion(s) 255a-c are shown (i.e., those portions 255a-c are visible in the 3-D images 250a-c that would otherwise be obstructed by the heart wall). As discussed above, the portion of the catheter 100 that would otherwise be obstructed by the heart wall may be identified by the enhancement component by comparing a depth coordinate of the catheter 100 to a depth coordinate of the surface of the heart 10, and then overlaying silhouettes 255a-c representing the obstructed portion(s) of the catheter 100 only when the depth coordinate of the catheter 100 is greater than the depth coordinate for the surface of the heart 10.

In FIGS. 6B and 6C it is further seen that more than one catheter 100 and 100' is shown in the 3-D images 250a-c. However, the rendering of the obstructed portion(s) 255b, 255c (respectively) are shown for the active catheter (i.e., the catheter that the physician is currently moving). In other embodiments, however, a graphical rendering may be shown for the obstructed portion(s) of more than one of the catheters (e.g., for both catheters 100 and 100').

It is noted that in FIG. 6A-C, the unobstructed portions 252a-c of the catheters are shown as being shaded so as to appear as a three-dimensional object, and the obstructed portions 252a-c are shown as silhouettes or outlines. However, any suitable differentiation may be used, such as but not limited to, different colors or different shading for the portions 252a-c and 255a-c.

Before continuing, it is also noted that in each of these images 250a-c, the output may be updated in real-time or substantially in real-time. Accordingly, the physician is able to view the images 250a-c as the catheter 100 is being moved and positioned at the desired location within the heart 10.

Figure 7:
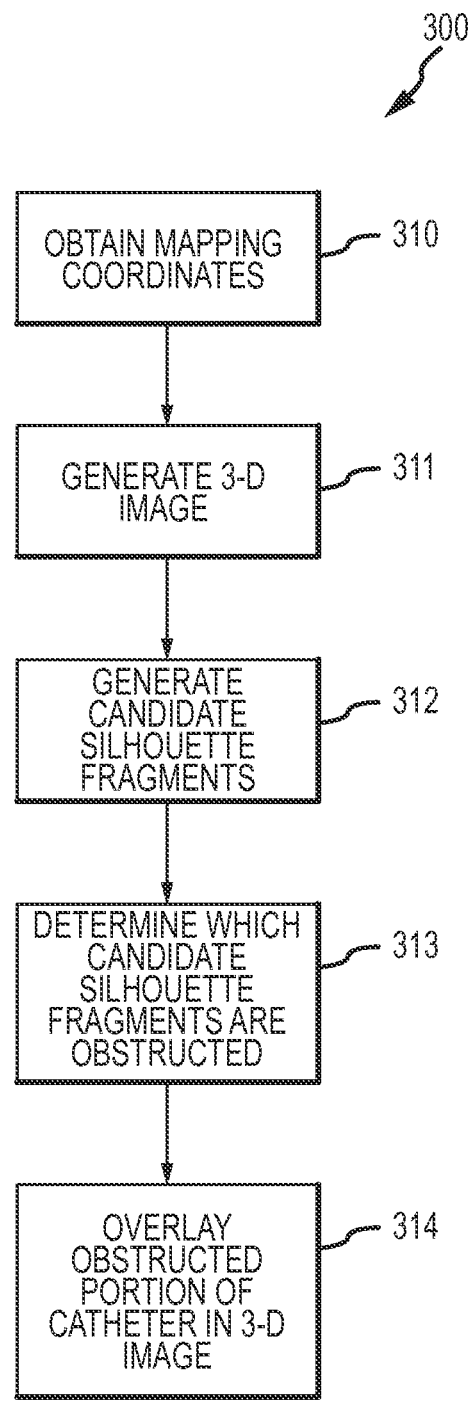
FIG. 7 is a flow diagram illustrating exemplary operations which may be implemented in accordance with the present invention.

FIG. 7 is a flow diagram illustrating exemplary operations which may be implemented in accordance with the present invention. Operations 300 may be embodied as logic instructions on one or more computer-readable medium. When executed on a processor, the logic instructions cause a general purpose computing device to be programmed as a special-purpose machine that implements the described operations. In an exemplary implementation, the components and connections depicted in the figures may be used for brokering creative content online.

Operations 300 illustrate an exemplary method for mapping cardiac tissue and modeling an obstructed view of an electrode catheter. In operation 310, mapping coordinates are obtained from an electrode catheter inserted into a chamber of a heart, where the mapping coordinates representing a surface of the heart. In operation 311, a three-dimensional image is generated based on the mapping information, where the three-dimensional image shows the surface of the heart and an unobstructed portion of the electrode catheter. In operation 312, a plurality of candidate silhouette fragments is generated representing a body of the electrode catheter. In operation 313, a determination is made which candidate silhouette fragments are obstructed by other visible objects in the three-dimensional image. And in operation 314, the obstructed portion of the electrode catheter is overlaid on the three-dimensional image using only those candidate silhouette fragments determined to be obstructed by other visible objects in the three-dimensional image.

The operations shown in FIG. 7 and described herein are provided for purposes of illustration. It is noted that the operations are not limited to the ordering shown. Still other operations may also be implemented.

Although exemplary embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical navigation and mapping system, comprising:
a rendering component operatively associated with an output device, the rendering component configured to receive position data associated with a catheter body of a catheter and overlay a plurality of data images on one another to generate a three-dimensional image representing both internal tissue and a visible portion of the catheter body; and
an enhancement component configured to overlay a silhouette on the three-dimensional image, the silhouette representing an obstructed portion of the catheter body using the positional data associated with the catheter body.

2. The system of claim 1, wherein the enhancement component generates candidate silhouette fragments and displays only those candidate silhouette fragments obstructed by other visible objects.

3. The system of claim 2, wherein other visible objects include portions of the internal tissue.

4. The system of claim 2, wherein other visible objects include display graphics.

5. The system of claim 2, wherein other visible objects include labels, lesions, anatomical markers, and other catheters.

6. The system of claim 1, wherein the enhancement component overlays a silhouette on the three-dimensional image of the obstructed portion of a plurality of catheters.

7. The system of claim 1, wherein the enhancement component graphically illustrates an outer boundary of the obstructed portion of the catheter body.

8. The system of claim 1, wherein the enhancement component applies a depth buffer to identify an outer boundary of the obstructed portion of the catheter body.

9. The system of claim 8, wherein the enhancement component only draws the outer boundary of the obstructed portion of the catheter body if a depth coordinate of the catheter body is greater than a depth coordinate for the internal tissue being shown.

10. The system of claim 1, wherein the silhouette representing the obstructed portion of the catheter body is shown as a different color or shading than a color or shading of an unobstructed portion of the catheter body.

11. The system of claim 1, wherein the silhouette representing the obstructed portion of the catheter body is shown in outline form and an unobstructed portion of the catheter body is shown in solid form.

12. A medical navigation and mapping system, comprising:
- a rendering component configured to generate a three-dimensional image based on mapping information associated with a catheter body of a catheter and internal tissue, the three-dimensional image representing an outer boundary of the internal tissue and a visible portion of the catheter body relative to the outer boundary of the internal tissue; and
- an enhancement component configured to overlay a silhouette of an obstructed portion of the catheter body on the three-dimensional image.

13. The catheter system of claim 12, wherein the enhancement component generates a plurality of candidate silhouette fragments representing the catheter body, and the enhancement component only displays the candidate silhouette fragments obstructed by other visible objects.

14. The catheter system of claim 13, wherein other visible objects include at least one of the following: portions of the internal tissue, lesions on the internal tissue, display graphics, anatomical markers, and other catheters.

15. The catheter system of claim 12, wherein the enhancement component graphically illustrates only an outer boundary of the obstructed portion of the catheter body in the three-dimensional image.

16. The catheter system of claim 12, wherein the enhancement component applies a depth buffer to identify the obstructed portion of the catheter body.

17. The catheter system of claim 12, wherein the enhancement component overlays the obstructed portion of the catheter body only when a depth coordinate of the catheter body is greater than a depth coordinate for the internal tissue being shown.

18. A method for mapping cardiac tissue and graphically illustrating both unobstructed and obstructed portions of an electrode catheter, comprising:
- obtaining mapping coordinates from an electrode catheter inserted into a chamber of a heart, the mapping coordinates representing a surface of the heart;
- generating a three-dimensional image based on the mapping information, the three-dimensional image showing the surface of the heart and a visible portion of the electrode catheter;
- generating a plurality of candidate silhouette fragments representing a body of the electrode catheter;
- determining which candidate silhouette fragments are obstructed by other visible objects in the three-dimensional image; and
- overlaying a silhouette of at least one obstructed portion of the electrode catheter using only those candidate silhouette fragments obstructed by other visible objects in the three-dimensional image.

19. The method of claim 18, further comprising applying a depth buffer to identify the at least one obstructed portion of the catheter body.

20. The method of claim 18, further comprising:
- comparing a depth coordinate of the electrode catheter to a depth coordinate of the surface of the heart; and
- overlaying the silhouette representing the at least one obstructed portion of the electrode catheter only when the depth coordinate of the electrode catheter is greater than the depth coordinate for the surface of the heart.

* * * * *